(12) United States Patent
Lim

(10) Patent No.: US 7,256,303 B1
(45) Date of Patent: Aug. 14, 2007

(54) METHOD FOR PRODUCING ALKYLATED CYCLOPENTADIENYL MANGANESE TRICARBONYLS

(76) Inventor: Tee Keng Lim, 111, Somerset Road #09-05, Singapore Power Building, Singapore (SG) 238164

( * ) Notice: Subject to any disclaimer, the term of this patent is extended or adjusted under 35 U.S.C. 154(b) by 0 days.

(21) Appl. No.: 11/671,011

(22) Filed: Feb. 5, 2007

(51) Int. Cl.
*C07F 13/00* (2006.01)

(52) U.S. Cl. ............................................... 556/47
(58) Field of Classification Search .................... 556/47
See application file for complete search history.

(56) References Cited

U.S. PATENT DOCUMENTS

| | | | | |
|---|---|---|---|---|
| 2,916,506 A | * | 12/1959 | Axtell et al. | 556/47 |
| 2,927,935 A | * | 3/1960 | Coffield et al. | 556/47 |
| 2,960,514 A | * | 11/1960 | Brown et al. | 556/47 |
| 2,964,547 A | * | 12/1960 | De Witt et al. | 556/47 |
| 2,987,529 A | * | 6/1961 | Sims | 556/47 |
| 2,987,530 A | * | 6/1961 | Pearson et al. | 556/47 |
| 3,040,077 A | * | 6/1962 | Freeman, Jr. | 556/47 |
| 4,699,987 A | * | 10/1987 | Gassman et al. | 556/1 |
| 4,946,975 A | * | 8/1990 | Wu et al. | 556/47 |
| 5,026,885 A | * | 6/1991 | Bell et al. | 556/47 |
| 5,281,733 A | * | 1/1994 | Inabinet et al. | 556/47 |

FOREIGN PATENT DOCUMENTS

| | | | |
|---|---|---|---|
| CH | 971221537 | | 6/1999 |
| CN | 1220268 A | * | 6/1999 |

* cited by examiner

*Primary Examiner*—Porfirio Nazario-Gonzalez
(74) *Attorney, Agent, or Firm*—John H. Thomas, P.C.

(57) ABSTRACT

A method for producing alkylated cyclopentadienyl manganese tricarbonyls, in particular a method for producing methyl cyclopentadienyl manganese tricarbonyl. It involves a process for synthesizing organometallic compounds. Alkylated cyclopentadienyl manganese tricarbonyls are antiknock additives used in engine fuels.

10 Claims, 2 Drawing Sheets

METHOD FOR PRODUCING ALKYLATED CYCLOPENTADIENYL MANGANESE TRICARBONYLS

This application claims the benefit and priority of China Patent Application No. 200610137411.0, filed Oct. 18, 2006.

TECHNICAL FIELD

The current invention involves a method for producing alkylated cyclopentadienyl manganese tricarbonyls. More specifically, it involves a process for synthesizing organometallic compounds, in particular a method for producing methyl cyclopentadienyl manganese tricarbonyl. Alkylated cyclopentadienyl manganese tricarbonyls are antiknock additives used in engine fuels.

BACKGROUND TECHNOLOGY

Alkylated cyclopentadienyl manganese tricarbonyls are antiknock additives, with methyl cyclopentadienyl manganese tricarbonyl (MMT) being the most widely used. Registered Chinese Patent No. 97122153 discloses a method for producing cyclopentadienyl manganese tricarbonyl. However, the cyclopentadienyl manganese tricarbonyl produced by that method is a crystalline salt. The use of a crystalline salt as an antiknock additive in a liquid poses certain problems. Its dissolution in the solvent is a problem which must be solved in the process.

Furthermore, during the course of producing alkylated cyclopentadienyl manganese tricarbonyl, it is often unavoidable to generate by-products such as cyclopentadienyl manganese tricarbonyl (CMT). Removing the CMT by-product requires further equipment and expense. However, the method of producing alkylated cyclopentadienyl manganese tricarbonyl involved in the current invention is characterized in that it does not require the removal of the CMT by-product. A small quantity of CMT in a mixture with alkylated cyclopentadienyl manganese tricarbonyl produces an unexpected octane synergism.

SUMMARY

The current invention discloses a simple, efficient, practical, and production-suitable method for producing alkylated cyclopentadienyl manganese tricarbonyls. More specifically, the current invention involves a method for producing a fuel antiknock additive, wherein the additive is an alkylated cyclopentadienyl manganese tricarbonyl. Preferably, "alkylated" in the current invention means mono- or poly-substituting cyclopentadiene groups with branched or unbranched alkyl groups containing 1 to 4 carbon atoms. More preferably, the alkylated cyclopentadiene in the current invention is selected from the group consisting of methyl cyclopentadiene, dimethyl cyclopentadiene, trimethyl cyclopentadiene, tetramethyl cyclopentadiene, ethyl cyclopentadiene, diethyl cyclopentadiene, triethyl cyclopentadiene, tetraethyl cyclopentadiene, propyl cyclopentadiene, dipropyl cyclopentadiene, tripropyl cyclopentadiene, tetrapropyl cyclopentadiene, butyl cyclopentadiene, dibutyl cyclopentadiene, tributyl cyclopentadiene, and tetrabutyl cyclopentadiene, and mixtures thereof. Particularly preferably, the current invention involves a method for producing methyl cyclopentadienyl manganese tricarbonyl (MMT).

DETAILED DESCRIPTION

Figure 1:
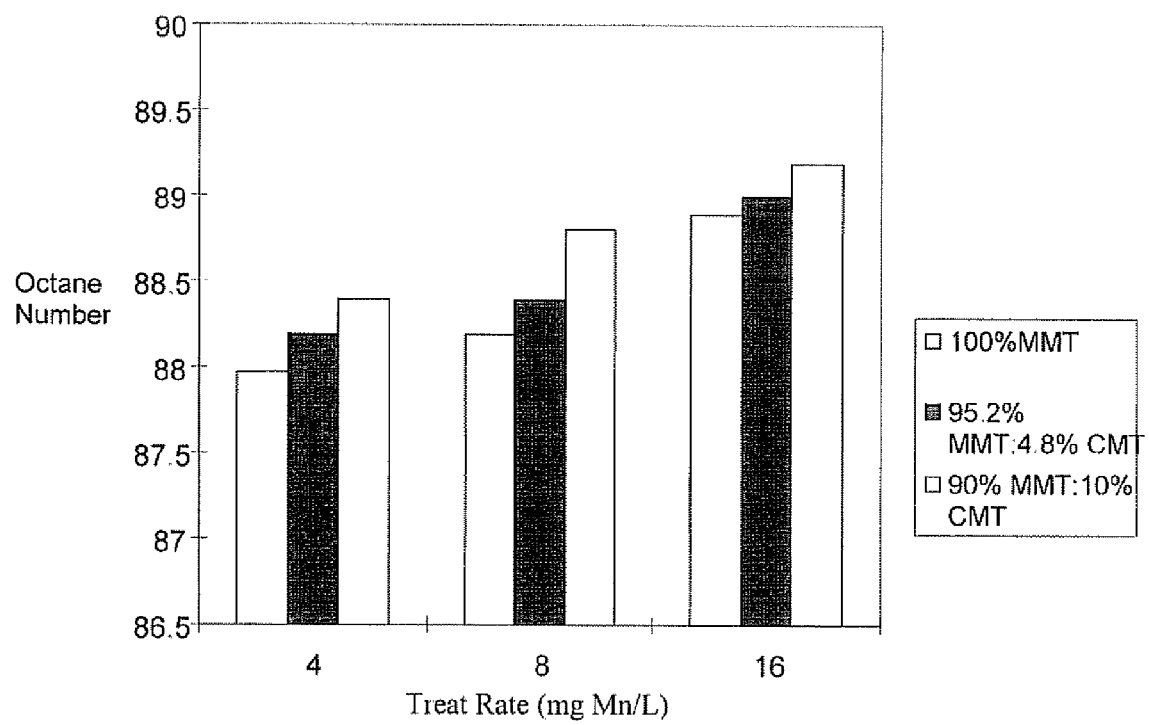
FIG. 1. An octane number response curve graph illustrating the effect of different ratios of MMT/CMT mixtures on the octane number.

The current invention involves a method for producing alkylated cyclopentadienyl manganese tricarbonyls, characterized in that the raw material used can be a mono- or poly-substituted cyclopentadiene wherein each substituent group is a branched or unbranched alkyl group containing 1 to 4 carbon atoms. In particular, the alkylated cyclopentadiene in the current invention is selected from the group consisting of methyl cyclopentadiene, dimethyl cyclopentadiene, trimethyl cyclopentadiene, tetramethyl cyclopentadiene, ethyl cyclopentadiene, diethyl cyclopentadiene, triethyl cyclopentadiene, tetraethyl cyclopentadiene, propyl cyclopentadiene, dipropyl cyclopentadiene, tripropyl cyclopentadiene, tetrapropyl cyclopentadiene, butyl cyclopentadiene, dibutyl cyclopentadiene, tributyl cyclopentadiene, and tetrabutyl cyclopentadiene, and mixtures thereof. Particularly preferably, the alkylated cyclopentadiene in the current invention is methyl cyclopentadiene and the alkylated cyclopentadienyl manganese tricarbonyl produced therefrom is methyl cyclopentadienyl manganese tricarbonyl (MMT).

According to one embodiment of the current invention, an alkylated cyclopentadienyl manganese tricarbonyl is produced by the following method:

(1) selecting a reaction kettle with a stirring device, a heating device, and a reaction solvent medium in which a reaction occurs in an inert gas atmosphere;

(2) injecting required amounts of reaction solvent medium and metal sodium into the kettle, so that the reaction process occurs in the inert gas atmosphere;

(3) adding alkylated cyclopentadiene into the kettle to form a reaction mixture;

(4) stirring the reaction mixture, wherein a halt in the release of hydrogen indicates that the reaction is complete and that alkylated cyclopentadienyl sodium has been produced;

(5) at room temperature, adding into the kettle manganese chloride and iron sulfonate dicarbonyl or iron phosphonate dicarbonyl, stirring and heating, then filling the kettle with CO to a pressure of at least 80-100 atm, heating the reaction mixture to a temperature sufficient to complete the reaction;

(6) when CO is no longer absorbed, which indicates that the reaction process is completed, stopping the heating, continuing to stir while cooling to room temperature, unloading the reaction mixture from the reaction kettle and obtaining a raw product. The cyclopentadienyl manganese tricarbonyl by-product is present in an quantity of 1.5% to 15%.

Based on step (5) of the foregoing embodiment of the invention, at room temperature, after adding manganese chloride and iron sulfonate dicarbonyl (or manganese chloride and iron phosphonate dicarbonyl), filling the kettle with CO, stirring the reactant mixture and heating it to a temperature sufficient to complete the reaction, with the preferred final temperature for the reaction mixture being between 200° C. and 500° C., more preferably between 240° C. and 300° C., and most preferably between 250° and 260°

C. As for the stirring speed, the relative stirring speed of the solid phase and liquid phase in the reaction solvent medium should not be less than 10 m/s or, the total stirring speed of the reaction mixture should be between 50 and 400 revolutions per minute.

According to another embodiment of the current invention, the foregoing method of producing alkylated cyclopentadienyl manganese tricarbonyls further comprises the step of refining the raw product by vacuum distillation at a temperature of between 30° C. and 80° C.

The reaction solvent medium used in the current invention can be tetrahydrofuran or diglyme, or, alternatively, other solvent mediums suitable for use in the production of organometallic antiknock agents which is familiar to a persons skilled in the art. The equipment that is suitable for use in the current invention may be the equipment disclosed in registered Chinese Patent No. 97122153 or other equipment with a stirring device and heater that is suitable for use in the production of organometallic antiknock agents. The content of Chinese Patent No. 97122153 is incorporated herein in its entirety in support and explanation of the current invention.

One of the advantages of the current invention lies in its providing a method for producing alkylated cyclopentadienyl manganese tricarbonyls with a rapid carbonylation reaction process, high product recovery rate, short production cycle, and improvements to the processing of the product and the mechanical stirring step.

Another advantage of the current invention is that the alkylated cyclopentadienyl manganese tricarbonyl produced is in the liquid form, therefore its solubility and mixability as an antiknock additive with other additives are increased, rendering the product more convenient to use. The final product of the existing cyclopentadienyl manganese tricarbonyl producing technology, i.e. cyclopentadienyl manganese tricarbonyl, is a crystalline salt that must be dissolved in a solvent before it can be used. The finished product of the current invention, i.e. alkylated cyclopentadienyl manganese tricarbonyl, is a liquid whose solubility and mixability as an additive are superior to those of cyclopentadienyl manganese tricarbonyl. Accordingly, the current invention solves the problem that the crystalline salt form of cyclopentadienyl tricarbonyl is difficult to be used directly.

Another advantage of the current invention lies in its ability to produce a combustion improving mixtures of alkylated cyclopentadienyl manganese tricarbonyl and cyclopentadienyl manganese tricarbonyl which have the unexpected effect of increasing the octane number of fuel. More specifically, the production of cyclopentadienyl manganese tricarbonyl is often unavoidable in the process of producing alkylated cyclopentadienyl manganese tricarbonyl, and removing the cyclopentadienyl manganese tricarbonyl requires additional steps and equipment, thereby increasing production times and expenditures. With the current invention, it was discovered that a mixture of alkylated cyclopentadienyl manganese tricarbonyl with a certain ratio of cyclopentadienyl manganese tricarbonyl produced an unexpected combustion improving effect, namely, that the octane enhancing effect of the mixture is superior to that of either alkylated cyclopentadienyl manganese tricarbonyl or cyclopentadienyl manganese tricarbonyl alone. Furthermore, as alkylated cyclopentadienyl manganese tricarbonyls can efficiently dissolve the cyclopentadienyl manganese tricarbonyl by-product produced during the production process, there is no need to provide another solvent to dissolve the cyclopentadienyl manganese tricarbonyl. Accordingly, based on the production method for the current invention, the alkylated cyclopentadienyl manganese tricarbonyl and cyclopentadienyl manganese tricarbonyl mixture can be produced in one go. In other words, the current invention not only does not require the use of more equipment and expenses to remove the cyclopentadienyl manganese tricarbonyl but it also does not require the provision of another solvent to dissolve the cyclopentadienyl manganese tricarbonyl, making the use of the current invention in industry more economical and efficient.

SPECIFIC EXAMPLES

Example 1

(1) Select a 6 liter reaction kettle with a stirring device and a heater for the reaction.
(2) Purge the reaction kettle with the inert gas CO, add 3.3 liters of tetrahydrofuran and 253 grams of metallic sodium, which will be in suspension status in the tetrahydrofuran. Repetitively purge with inert gas.
(3) Start stirring slowly (with a stirring speed of the solid phase and liquid phase in the reaction medium of 0.01 m/s). At a temperature of less than 10° C., add 780 grams of methyl cyclopentadiene. The halt in the release of hydrogen indicates that the reaction process is complete and that methyl cyclopentadienyl sodium has been produced.
(4) At room temperature, in suspension status, add a mixture comprising 700 grams of manganese chloride and 10.3 grams (0.1 mol) of iron sulfonate dicarbonyl to the solvent tetrahydrofuran, stir, heat to 60° C. and then add CO to the reaction kettle to pressurize it to 80 atm. Increase the temperature to between 250° C. and 260° C. Stir the reaction mixture at a relative speed for its solid phase and liquid phase of not less than 10 m/s. After 15 minutes, the pressure drop in the reaction kettle stops, indicating that the reaction mixture has ceased absorbing CO and that the carbonylation reaction is complete
(5) Lower the temperature and cease stirring. When the temperature of the reaction mixture reaches room temperature, remove the reaction product from the reaction kettle, thus obtaining the raw product of the current invention, methyl cyclopentadienyl manganese tricarbonyl.

Separate out the refined product through vacuum distillation of the raw product methyl cyclopentadienyl manganese tricarbonyl at a temperature of 80° C. to 95° C., obtaining methyl cyclopentadienyl manganese tricarbonyl in a liquid form.

Example 2

Mixtures of methyl cyclopentadienyl manganese tricarbonyl (MMT) and cyclopentadienyl manganese tricarbonyl (CMT) mixed in different ratios were tested with the ASTM-CFR test engine in accordance with the international standard ASTM D2699. The effect of the different mixtures on the octane number of regular unleaded gasoline was recorded at equal manganese levels.

Figure 2:
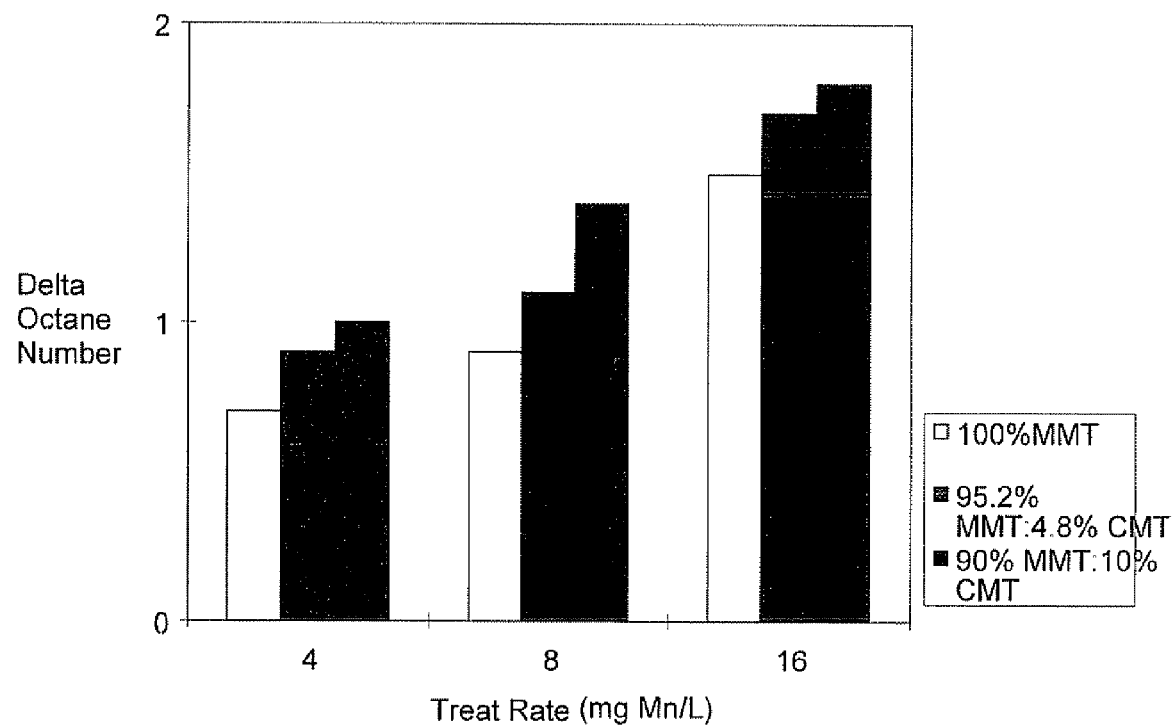
FIG. 2. A delta octane number curve graph illustrating the effect of different ratios of MMT/CMT mixtures on the delta octane number change from base fuel

FIG. 1 shows the effect on the octane number at each manganese treat rate of MMT/CMT mixtures mixed in different ratios FIG. 2 shows the effect on the change (delta) in octane number at each manganese treat rate of MMT/CMT mixtures mixed in different percentages as compared to the unadditized base fuel. As the figures show, a mixture of approximately 10% CMT and 90% MMT at an 8 mg Mn/L treat rate produces an unexpected synergism, with a delta octane number of 1.4 (FIG. 2). This represents a 56% strengthening of the effect as compared to the 0.9 delta octane number produced by using MMT alone.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

That which is claimed is:

1. A method for producing alkylated cyclopentadienyl manganese tricarbonyls, comprising the steps of:
    (1) selecting a reaction kettle with a stirring device, a heating devise, and a reaction solvent medium in which a reaction occurs in an inert gas atmosphere;
    (2) injecting required amounts of reaction solvent medium and metal sodium into the kettle, so that the reaction process occurs in the inert gas atmosphere;
    (3) adding alkylated cyclopentadiene into the kettle to form a reaction mixture;
    (4) stirring the reaction mixture, wherein a halt in the release of hydrogen indicates that the reaction is complete and that alkylated cyclopentadienyl sodium has been produced;
    (5) at room temperature, adding into the kettle manganese chloride and iron sulfonate dicarbonyl or iron phosphonate dicarbonyl, stirring and eating, then filling the kettle with CO, pressurizing the kettle to at least 80-100 atm with CO, heating the reaction mixture to a temperature sufficient to complete the reaction,
    (6) when CO is no longer absorbed, which indicates that the reaction process is completed, stopping the heating, continuing to stir while cooling to room temperature, unloading the reaction mixture from the reaction kettle and obtaining a raw product.

2. The method of claim 1 for producing alkylated cyclopentadienyl manganese tricarbonyls, further comprising the step of refining the raw product by vacuum distillation at a temperature of 30-80° C.

3. The method of claim 1 for producing alkylated cyclopentadienyl manganese tricarbonyls, wherein the alkylated cyclopentadiene is selected from the group consisting of methyl cyclopentadiene, dimethyl cyclopentadiene, trimethyl cyclopentadiene, tetramethyl cyclopentadiene, ethyl cyclopentadiene, diethyl cyclopentadiene, triethyl cyclopentadiene, tetraethyl cyclopentadiene, propyl cyclopentadiene, dipropyl cyclopentadiene, tripropyl cyclopentadiene, tetrapropyl cyclopentadiene, butyl cyclopentadiene, dibutyl cyclopentadiene, tributyl cyclopentadiene, and tetrabutyl cyclopentadiene, and mixtures thereof.

4. The method of claim 1 for producing alkylated cyclopentadienyl manganese tricarbonyls, wherein the alkylated cyclopentadiene is methyl cyclopentadiene.

5. The method of claim 1 for producing alkylated cyclopentadienyl manganese tricarbonyls, wherein the reaction solvent medium is tetrahydrofuran or diglyme.

6. The method of claim 1 for producing alkylated cyclopentadienyl manganese tricarbonyls, wherein the relative stirring speed of the solid phase and liquid phase in the reactant mixture should not be less than 10 m/s.

7. The method of claim 1 for producing alkylated cyclopentadienyl manganese tricarbonyls, wherein the total stirring speed of the reaction mixture is between 50 and 400 revolutions per minute.

8. The method of claim 1 for producing alkylated cyclopentadienyl manganese tricarbonyls, wherein the reactant mixture is heated to between 200° C. and 500° C.

9. The method of claim 8 for producing alkylated cyclopentadienyl manganese tricarbonyls, wherein the reaction mixture is heated to between 240° C. and 300° C.

10. The method of claim 9 for producing alkylated cyclopentadienyl manganese tricarbonyls, wherein the reaction mixture is heated to between 250° C. and 260° C.

* * * * *